US006730515B2

(12) United States Patent
Kocher

(10) Patent No.: US 6,730,515 B2
(45) Date of Patent: May 4, 2004

(54) MICRO-ARRAY CALIBRATION MEANS

(75) Inventor: Thomas E. Kocher, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 16 days.

(21) Appl. No.: 10/167,245

(22) Filed: Jun. 11, 2002

(65) Prior Publication Data

US 2003/0228697 A1 Dec. 11, 2003

(51) Int. Cl.$^7$ ................................................ G01N 31/00
(52) U.S. Cl. ........................ 436/8; 436/164; 436/172; 435/DIG. 22; 435/DIG. 43
(58) Field of Search ...................... 436/8, 164, 172; 435/4, DIG. 22, DIG. 43, 6

(56) References Cited

U.S. PATENT DOCUMENTS

| | | |
|---|---|---|
| 5,412,087 A | 5/1995 | McGall et al. |
| 5,489,678 A | 2/1996 | Fodor et al. |
| 5,981,180 A | 11/1999 | Chandler et al. |
| 6,023,540 A | 2/2000 | Walt et al. |
| 6,079,283 A | 6/2000 | Papen et al. |
| 6,083,762 A | 7/2000 | Papen et al. |
| 6,094,966 A | 8/2000 | Papen et al. |
| 6,429,027 B1 * | 8/2002 | Chee et al. .................. 436/518 |
| 2001/0029049 A1 * | 10/2001 | Walt et al. .................. 436/518 |
| 2002/0090613 A1 * | 7/2002 | Seul et al. ...................... 435/6 |
| 2003/0027214 A1 * | 2/2003 | Kamb .......................... 435/7.1 |
| 2003/0068609 A1 * | 4/2003 | Chari et al. ..................... 435/4 |
| 2003/0108453 A1 * | 6/2003 | Nguyen et al. .............. 422/102 |
| 2003/0143542 A1 * | 7/2003 | Qiao et al. ...................... 435/6 |

FOREIGN PATENT DOCUMENTS

| WO | 99/67641 | * 12/1999 |
|---|---|---|
| WO | 01/98765 | * 12/2001 |

OTHER PUBLICATIONS

2001 Nature Biotechnology, "Quantum–dot–tagged micro-beads for multiplexed optical coding of biomolecules", Mingyong Han, Xiaohu Gao, Jack Z. Su, Shuming Nie, Jul. 2001, vol. 19.

Science–research article, "Light–Directed, Spatially Addressable Parallel Chemical Synthesis", Stephen P.A. Fodor, J. Leighton Read, Michael C. Pirrung, Lubert Stryer, Amy Tsai Lu, Dennis Solas, Feb. 15, 1991.

* cited by examiner

*Primary Examiner*—Maureen M. Wallenhorst
(74) *Attorney, Agent, or Firm*—William F. Noral

(57) ABSTRACT

Apparatus calibrates a micro-array receiver. The apparatus includes a micro-array receiver including a substrate having coated a biologically active region with a composition including a first set of micro-spheres modified with a biological probe and containing an optical bar code generated from at least one colorant associated with the micro-spheres; and a calibration region associated with the substrate, the region being outside the biologically active region and having an area containing the optical bar code color.

6 Claims, 2 Drawing Sheets

MICRO-ARRAY CALIBRATION MEANS

FIELD OF THE INVENTION

This invention relates in general to molecular biological systems created with color beads and, more particularly to a means by which a micro-array reader can determine the colors used for encoding random beads.

BACKGROUND OF THE INVENTION

Ever since it was invented in the early 1990s (Science, 251, 767–773, 1991), high-density arrays formed by spatially addressable synthesis of bioactive probes on a 2-dimensional solid support has greatly enhanced and simplified the process of biological research and development. The key to current micro-array technology is deposition of a bioactive agent at a single spot on a microchip in a "spatially addressable" manner.

Current technologies have used various approaches to fabricate micro-arrays. For example, U.S. Pat. No. 5,412,087, issued May 2, 1995, McGall et al., and U.S. Pat. No. 5,489,678, issued Feb. 6, 1996, Fodor et al., demonstrate the use of a photolithographic process for making peptide and DNA micro-arrays. The patent teaches the use of photolabile protecting groups to prepare peptide and DNA micro-arrays through successive cycles of deprotecting a defined spot on a 1 cm×1 cm chip by photolithography, then flooding the entire surface with an activated amino acid or DNA base. Repetition of this process allows construction of a peptide or DNA micro-array with thousands of arbitrarily different peptides or oligonucleotide sequences at different spots on the array. This method is expensive. An inkjet approach is being used by others e.g., U.S. Pat. No. 6,079,283, issued Jun. 27, 2000, Papen et al., U.S. Pat. No. 6,083,762, issued Jul. 4, 2000, Papen et al., and U.S. Pat. No. 6,094,966, issued Aug. 1, 2000, Papen et al., to fabricate spatially addressable arrays, but this technique also suffers from high manufacturing cost in addition to the relatively large spot size of 40 to 100 $\mu$m. Because the number of bioactive probes to be placed on a single chip usually runs anywhere from 1000 to 100000 probes, the spatial addressing method is intrinsically expensive regardless how the chip is manufactured. An alternative approach to the spatially addressable method is the concept of using fluorescent dye-incorporated polymeric beads to produce biological multiplexed arrays. U.S. Pat. No. 5,981,180, issued Nov. 9, 1999, Chandler et al., discloses a method of using color coded beads in conjunction with flow cytometry to perform multiplexed biological assay. Micro-spheres conjugated with DNA or monoclonal antibody probes on their surfaces were dyed internally with various ratios of two distinct fluorescence dyes. Hundreds of "spectrally addressed" micro-spheres were allowed to react with a biological sample and the "liquid array" was analyzed by passing a single micro-sphere through a flow cytometry cell to decode sample information. U.S. Pat. No. 6,023,540, issued Feb. 8, 2000, Walt et al., discloses the use of fiber-optic bundles with pre-etched microwells at distal ends to assemble dye loaded micro-spheres. The surface of each spectrally addressed micro-sphere was attached with a unique bioactive agent and thousands of micro-spheres carrying different bioactive probes combined to form "beads array" on pre-etched microwells of fiber optical bundles. More recently, a novel optically encoded micro-sphere approach was accomplished by using different sized zinc sulfide-capped cadmium selenide nanocrystals incorporated into micro-spheres (Nature Biotech. 19, 631–635, (2001)). Given the narrow band width demonstrated by these nanocrystals, this approach significantly expands the spectral bar coding capacity in micro-spheres.

Even though the "spectrally addressed micro-sphere" approach does provide an advantage in terms of its simplicity over the old fashioned "spatially addressable" approach in micro-array making, there are still needs in the art to make the manufacture of biological micro-arrays less difficult and less expensive and to simplify the process for identifying the color spectrum used to encode the beads (micro-spheres) used in micro-array receivers.

SUMMARY OF THE INVENTION

According to the present invention, there is provided a solution to the problems and fulfillment of the needs discussed above.

According to a feature of the present invention, there is provided an apparatus for calibrating a micro-array receiver comprising;

a micro-array receiver including a substrate having coated a biologically active region with a composition including a first set of micro-spheres modified with a biological probe and containing an optical bar code generated from at least one colorant associated with said micro-spheres; and a calibration region associated with said substrate, said region being outside said biologically active region and having an area containing said optical bar code color.

ADVANTAGEOUS EFFECT OF THE INVENTION

The invention has the following advantages.

1. A robust means is provided by which a micro-array reader can identify the color spectrum used to encode micro-spheres (beads) used in random array structures.
2. A calibration color region is provided on the micro-array receiver having identifying marks adjacent thereto to facilitate location of the calibration region by the micro-array reader.

DETAILED DESCRIPTION OF THE INVENTION

Figure 1:
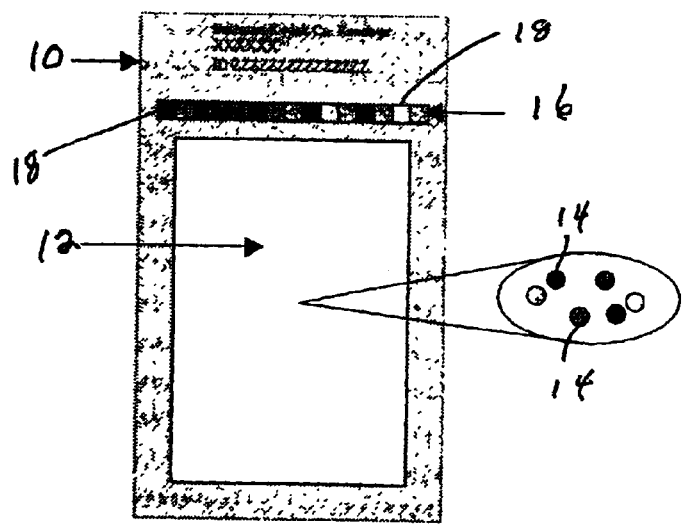
FIG. 1 is a diagrammatic view of an embodiment of the present invention.

In general, the present invention relates to a biological analysis system including a micro-array receiver having random or predetermined array of biologically functional sites which can form a repetitive pattern on the receiver. An exemplary micro-array receiver is described in U.S. patent application Ser. No. 09/942,241, Chari et al., the contents of which are hereby incorporated by reference. A general description of the micro-array receiver will now be given but reference is made to the latter patent application for a more complete description.

The micro-array receiver includes a substrate coated with a composition comprising micro-spheres (beads) dispersed in a fluid containing a gelling agent or a precursor to a gelling agent, wherein the micro-spheres are immobilized in a random or ordered position on the substrate. The substrate is free of receptors designed to physically or chemically interact with the micro-spheres. One or more sub-populations of the population of micro-spheres contain a unique optical bar code generated from at least one colorant associated with the micro-spheres and including a unique biological functionality or probe which react with analytes with which they come in contact.

The distribution or pattern of micro-spheres on the substrate may be entirely random (a spatial distribution showing no reference or bias) or be attracted or held to sites that are pre-marked or predetermined on the substrate. Each micro-sphere in the array has a distinct signature based on color which may be derived from mixing three dyes representing the primary colors Red (R), Green (G), and Blue (B) to create thousands of distinguishable micro-spheres with distinct color addresses (unique RGB values, e.g., R=0, G=204, B=153). The micro-spheres are made with active sites on their surface to which are attached a specific bioactive probe. Therefore, each color address can correspond to a specific bioactive probe.

A micro-array or population of micro-spheres can include a few or hundreds or more of sub-populations of micro-spheres, where each sub-population comprises the same color code and the same bio-active probe. Each micro-array of micro-spheres occupies a sub-area of the substrate and is repeated in a pattern over the area of the substrate. The dimensional area of the micro-array sub-area may be comparable to the dimensional area of a microtiter well or multiple wells may overlay a micro-array sub-area.

The micro-spheres are preferably coated onto the substrate as disclosed in U.S. patent application Ser. No. 09/942, 241, Chari et al.

In order to use a micro-array having bioactive probes to analyze an unknown biological target sample, the sample to be analyzed has to be nonselectively labeled by using fluorescent dyes or chemiluminescent active molecules.

A biological target sample is placed into contact with the micro-array bioactive probes. The fluorescently/chemiluminescently signals which result from the hybridization of the unknown biological target sample with bioactive probes on the surface of the coated micro-spheres are detected and analyzed by an electronic camera/image processor system.

The invention provides a robust means by which a micro-array reader can identify the color spectrum used to encode beads (micro-spheres) used in random array structures. The array reader will know, apriori, the color spectrum of the beads used to produce the array, and thus will be able to discern with greater accuracy the spectrum of the bead under investigation. An implementation may include a target that includes a region having a series of areas, each containing a specific bead color. The areas will be printed on the micro-array receiver, preferably in a linear array away from the diagnostic region. As envisioned, the reader will locate the calibration target through identifying datum(s) or fiducial mark(s) and determine the color spectrum of each region within the target. This concept provides a means to determine with high-accuracy the specific bead under investigation. The robust nature or higher-accuracy comes about because in a random array of colored beads, there is a finite probability that two or more beads will overlap (agglomerate). In this instance, the detector would integrate the signal from all the beads and produce a color signature that would be different from the signature of a stand alone one. With the calibration areas, software could determine the color signature from each unique color and combinations of each and could de-convolve the unique colors and thus identify the bead(s). Otherwise, in this instance, the agglomerated beads would have to be identified and ignored. This would reduce the diversity of the array.

It is understood that the calibration area would contain every color used to encode the beads and include small areas of these unique colors. Each area is preferably 500 um×500 um and more preferably 2 mm×2 mm. The areas can be created by various printing means including inkjet deposition.

Referring now to FIG. 1, there is shown an embodiment of the present invention. As shown, micro-array receiver 10 includes a biologically active area 12 containing colored beads 14 having attached biological probes distributed in a random or orderly way. Micro-array receiver 10 also includes, according to the invention, a calibration region 16 outside of said biologically active region 12. Region 16 includes a plurality of discrete color areas 18, each area containing one color corresponding to a color used in the colored beads. Thus, area 12 contains beads of fifteen different colors representing fifteen different biological probes, region 16 has fifteen areas 18 of fifteen colors matching the fifteen bead colors.

Figure 2:
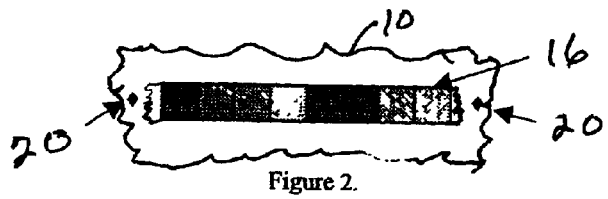
FIG. 2 is a diagrammatic view of another embodiment of the present invention.

As shown in FIG. 2, the calibration region 16 is provided with identifier(s) (marks) 20 adjacent to region 16 to facilitate location of region 16 by a micro-array receiver reader.

Region 16 can be placed anywhere on the front or back of receiver 10 outside the region of biological activity.

Figure 3:
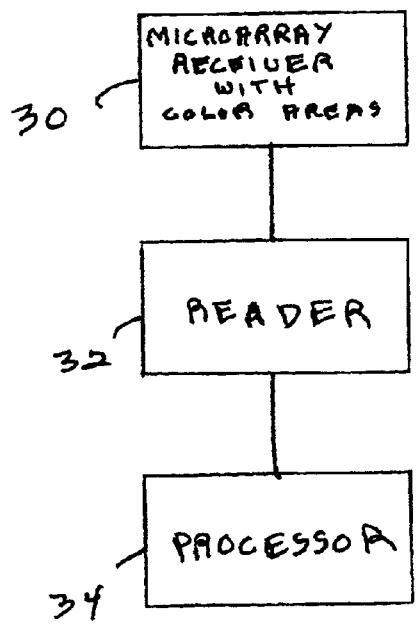
FIG. 3 is a block diagram of a system for utilizing the present invention.

FIG. 3 shows a block diagram of a system for utilizing the present invention. Block 30 represents a micro-array receiver after it has come into contact with a sample analyte containing one or more unknown biological targets that can hybridize biological probes on the receiver. Those probes that have been hybridized can be processed for luminescence or phosphorescence by reader 32. Reader 32 also reads the color areas 18 in calibration region 16 or receiver 12. Processor 34 can match the known colors from calibration region 16 with the colors read from the hybridized colored bead 14 to identify the unknown biological targets in the analyte.

Figure 4:
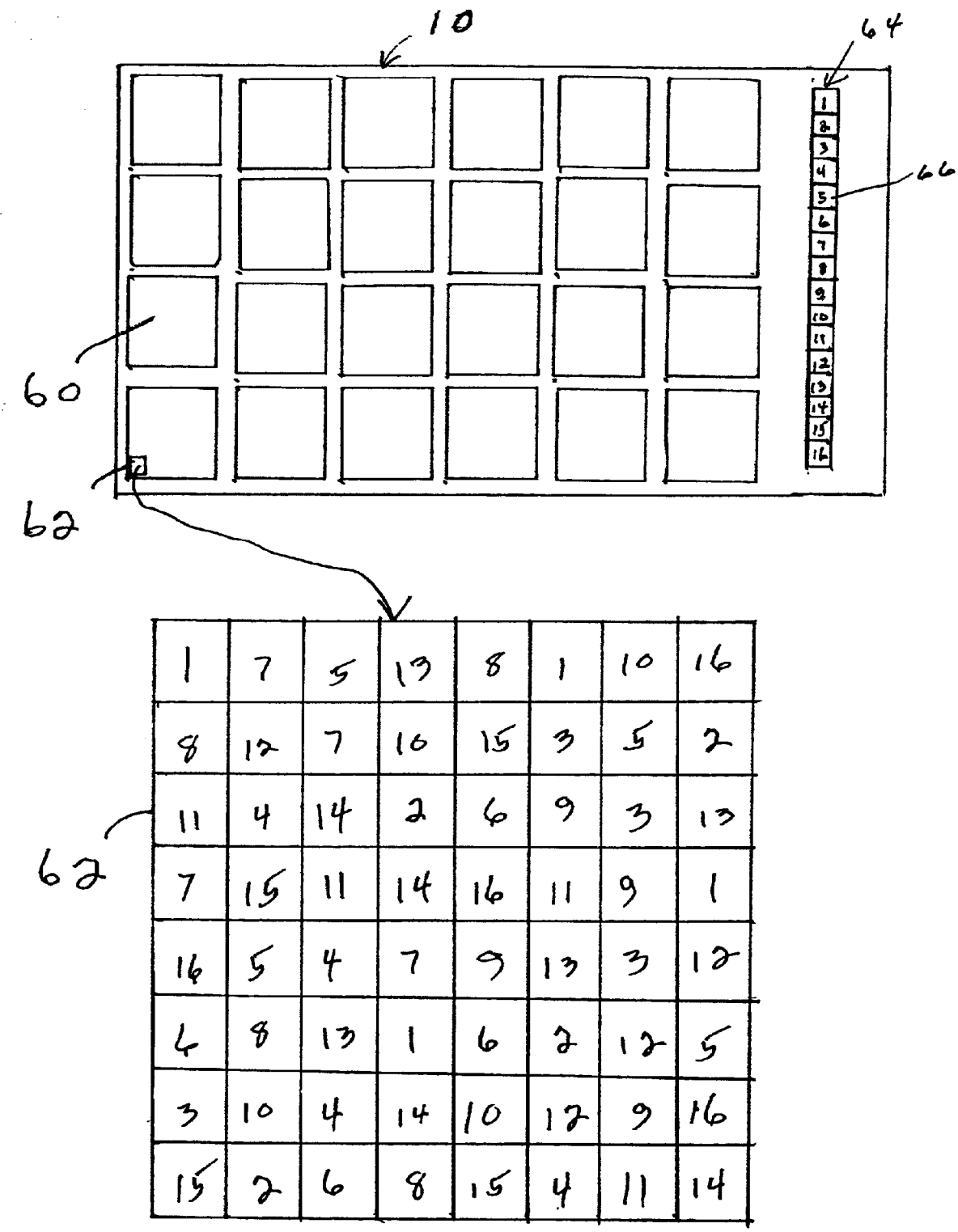
FIG. 4 is a diagrammatic view of another embodiment of the present invention.

FIG. 4 illustrates a micro-array receiver that can be used in the present invention. As shown, micro-array receiver 10 includes a pattern of 24 regions 60 in a matrix of 4 rows and 6 columns. Each region includes an identical micro-array of randomly distributed biological probe sites, a portion of which are shown in the exploded view. In this view, 16 different biological probes attached to micro-spheres are randomly distributed throughout the portion 62 of region 60. According to the invention, each probe is attached to a micro-sphere of a color unique to that probe so that micro-spheres of 16 different colors are present in portion 62. If, for example, an analyte containing each of the 16 complimentary targets to the 16 probes is brought into contact with portion 62, the hybridization of the 16 targets with the 16 probes would produce luminescence or fluorescence of 16 different colors which are detected by an appropriate detection system. Calibration region 64 includes sixteen areas 66 each of a color corresponding to the sixteen colors unique to the probes attached to the micro-spheres.

The invention has been described in detail with particular reference to certain preferred embodiments thereof, but it will be understood that variations and modifications can be effected within the spirit and scope of the invention.

PARTS LIST

- 10 micro-array receiver
- 12 biological active area
- 14 colored beads
- 16 calibration region
- 18 discrete color areas
- 20 identifiers marks
- 30 micro-array receiver with color beads
- 32 reader
- 34 processor
- 60 pattern of 24 regions
- 62 16 probes
- 64 calibration region
- 66 16 areas

What is claimed is:

1. Apparatus for calibrating a micro-array reader comprising;

a micro-array receiver including a substrate having a biologically active region coated with a composition including a first set of micro-spheres modified with a biological probe and containing an optical bar code generated from at least one colorant associated with said micro-spheres; and a calibration region associated with said substrate, said region being outside said biologically active region and having an area coated with said at least one optical bar code colorant;

wherein said microarray reader is calibrated at the time of biological sample testing by detection of a unique color signature of said at least one colorant in both the calibration region and the biologically active region.

2. The apparatus of claim 1 wherein said composition coated on said substrate includes a plurality of sets of micro-spheres each set being modified with a unique biological probe and containing a unique optical bar code generated from at least one colorant associated with said micro-spheres; and wherein said calibration region includes a plurality of discrete areas, each area containing one of said plurality of unique optical bar codes.

3. The apparatus of claim 2 wherein said plurality of sets of micro-spheres are randomly distributed throughout said biologically active region.

4. The apparatus of claim 2 wherein said calibration region includes a linear array of said discrete areas.

5. The apparatus of claim 1 including an identifier adjacent to said calibration region for identifying the location of said region.

6. The apparatus of claim 1 wherein said first set of micro-spheres are immobilized in a coating containing a gelling agent or precursor to a gelling agent.

* * * * *